United States Patent [19]

Ishizuka et al.

[11] Patent Number: 5,798,387
[45] Date of Patent: Aug. 25, 1998

[54] AMINO ACID DERIVATIVES

[75] Inventors: Masaaki Ishizuka, Mishima; Masaji Kawazu, Numazu; Toshiaki Katsumi; Yoshihide Fuse, both of Himeji; Kenji Maeda; Tomio Takeuchi, both of Tokyo, all of Japan

[73] Assignees: Zaidan Hojin Biseibutsu Kagaku Kenkyu Kai, Tokyo; Kanegafuchi Kagaku Kogyo Kabushiki Kaisha, Osaka, both of Japan

[21] Appl. No.: 753,381

[22] Filed: Nov. 25, 1996

Related U.S. Application Data

[63] Continuation of Ser. No. 244,810, Jun. 13, 1994, abandoned.

[30] Foreign Application Priority Data

Oct. 15, 1992 [JP] Japan .................................. 4-301559

[51] Int. Cl.$^6$ ...................................... A61K 31/22
[52] U.S. Cl. ........................... 514/551; 514/563; 562/567; 562/575; 560/170; 560/155
[58] Field of Search ...................... 562/567, 575; 560/170, 155; 514/551, 563

[56] References Cited

U.S. PATENT DOCUMENTS 3,855,238  12/1974  Batesky ............................. 260/326.14
4,565,653   1/1986  Ives et al. .

FOREIGN PATENT DOCUMENTS 62-56457  3/1987  Japan .
4-187664  7/1992  Japan .

OTHER PUBLICATIONS

Chemical Abstracts 115:15575; RN=134381-30-9P, 1990.
Chem Abstract 112:114678, 1989, rn=91694-75-6.
Beilstein Reg No. 1712631, 1951, rn=91694-75-6.

*Primary Examiner*—Samuel Barts
*Attorney, Agent, or Firm*—Larson & Taylor

[57] ABSTRACT

A novel amino acid derivative represented by the general formula (I) shown below or a salt thereof have now been provided by chemical synthesis, and it has been found that these new compounds stimulate proliferation and physiological activities of the T cells of mammals, have an immunomodulating activity and also have an antitumor activity or a carcinostatic activity. It has also been found that these new compounds have an effect of stimulating the proliferation of hematopoietic stem cells.

$$R^1-\underset{\underset{O}{\|}}{C}-\underset{\underset{R^2}{|}}{N}-\underset{\underset{R^3}{|}}{C}\underset{R^4}{\overset{(CH_2)_yCOR^5}{\diagup}} \quad (I)$$

wherein y is 0 or 1; $R^1$ represents an unsubstituted $C_1$–$C_8$ alkyl group or others;

$R^2$ represents a hydrogen atom, a $C_1$–$C_5$ alkyl group or others;

$R^3$ represents a hydrogen atom, a $C_1$–$C_8$ alkyl group or others;

$R^4$ represents a hydrogen atom, a $C_1$–$C_3$ alkyl group or others;

$R^5$ represents a group —$OR^{42}$, a group $$-N\underset{R^{44}}{\overset{R^{43}}{\diagup}}$$

or others.

7 Claims, No Drawings

AMINO ACID DERIVATIVES

This application is a continuation of application Ser. No. 08/244,810 filed Jun. 13, 1994 now abandoned which is a 371 of PCT/JP93/01482 filed Oct. 15, 1993.

TECHNICAL FIELD

This invention relates to novel amino acid derivatives which have immunomodulating activity, antitumor activity and/or hematopoietic stem cell-amplifying activity and are represented by the general formula (I) shown hereinafter, and also it relates to salts of salt-formable ones of said amino acid derivatives. Further, this invention relates to an immunomodulator comprising as active ingredient a novel amino acid derivative represented by the general formula (I) or a salt thereof, and an antitumor agent comprising as active ingredient a novel amino acid derivative represented by the general formula (I) or a salt thereof, as well as a hematopoietic stem cell amplifier comprising as active ingredient a novel amino acid derivative represented by the general formula (I) or a salt thereof.

BACKGROUND ART

Because many of antitumor agents which have heretofore been clinically used are inherently cytotoxic substances, they are accompanied by the drawbacks that they generally have strong toxicity, can give damages to normal cells along with their ability to prevent growth of cancer cells, and hence can induce strong side-effects. There is accordingly an outstanding demand for novel antitumor agents which have such a mechanism of the activity as different from that of the conventional antitumor agents, show low toxicity and weaker side-effects and are effective for therapeutic treatment of human tumors.

DISCLOSURE OF THE INVENTION

As a result of an extensive investigation, we, the present inventors, have succeeded in synthesizing novel amino acid derivatives which can be represented by the general formula (I) shown hereinafter, and we have also found that these amino acid derivatives stimulate activation of T cell of mammals and hence have one or more of the immunomodulating activity and the antitumor and/or carcinostatic activities against various tumors and/or cancers, as well as the hematopoietic stem cell-amplifying activity. Based on these findings, the present invention has been completed.

According to a first aspect of the present invention, therefore, there is provided a novel amino acid derivative of the hereinafter described formula (I) or a salt thereof, as a novel substance. This novel amino acid derivative according to the present invention is a compound which is represented by the following general formula (I), namely an amino acid derivative having the general formula (I):

wherein y stands for an integer of 0 or 1;

$R^1$ represents an unsubstituted $C_1$-$C_8$ alkyl group; or $R^1$ represents a $C_1$-$C_8$ alkyl group substituted by one to four substituents which may be the same or different and are each (i) a group represented by the formula —$OR^6$ in which $R^6$ denotes a hydrogen atom, a $C_1$-$C_3$ alkyl group or an acyl group represented by —$COR^7$ (where $R^7$ is a hydrogen atom, methyl group or ethyl group), or a group represented by

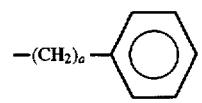

(where a is an integer of 0 to 3), (ii) a group represented by the formula

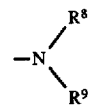

in which $R^8$ denotes a hydrogen atom, a $C_1$-$C_3$ alkyl group or an acyl group represented by —$COR^{10}$ (where $R^{10}$ is a hydrogen atom, methyl group or ethyl group), and $R^9$ denotes a hydrogen atom or a $C_1$-$C_3$ alkyl group, (iii) a group represented by the formula —$SR^{11}$ in which $R^{11}$ denotes a hydrogen atom or $C_1$-$C_3$ alkyl group, (iv) a group represented by the formula —$COR^{12}$ in which $R^{12}$ denotes a hydroxyl group or a group represented by —$OR^{13}$ (where $R^{13}$ is a $C_1$-$C_3$ alkyl group), or (v) a phenyl group;

or $R^1$ represents a $C_1$-$C_8$ alkyl group substituted by hydroxyl group(s) and amino group(s);

$R^2$ represents a hydrogen atom, a $C_1$-$C_5$ alkyl group, or a group represented by the formula

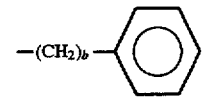

where b is an integer of 0 to 3);

$R^3$ represents (i) a hydrogen atom, (ii) a $C_1$-$C_8$ alkyl group, (iii) a $C_1$-$C_4$ alkenyl group, or (iv) a group represented by the formula —$(CH_2)_c$—$R^{14}$ in which $R^{14}$ denotes a group represented by —$OR^{15}$ (where $R^{15}$ is a hydrogen atom, a $C_1$-$C_3$ alkyl group or a group represented by

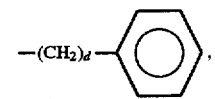

d being an integer of 0 to 3, or $R^{15}$ is a group represented by —$COR^{16}$, $R^{16}$ being a hydrogen atom, methyl group or ethyl group); or $R^{14}$ denotes a group represented by —$SR^{17}$ (where $R^{17}$ is a hydrogen atom, a $C_1$-$C_3$ alkyl group or a group represented by

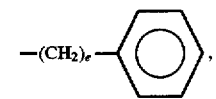

e being an integer of 0 to 2); or $R^{14}$ denotes a group represented by —$SO_2R^{18}$ (where $R^{18}$ is a group represented by —$OR^{19}$, $R^{19}$ being a hydrogen atom or a $C_1$-$C_3$ alkyl group, or $R^{18}$ is a group represented by

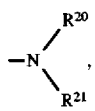

$R^{20}$ and $R^{21}$ independently being a hydrogen atom or a $C_1$–$C_3$ alkyl group); or $R^{14}$ denotes a group represented by —$COR^{22}$ (where $R^{22}$ is a group represented by —$OR^{23}$, $R^{23}$ being a hydrogen atom or a $C_1$–$C_3$ alkyl group, or $R^{22}$ is a group represented by

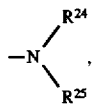

and $R^{25}$ independently being a hydrogen atom or a $C_1$–$C_3$ alkyl group); or $R^{14}$ denotes a group represented by

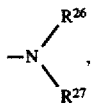

$R^{26}$ and $R^{27}$ independently being a hydrogen atom or a $C_1$–$C_3$ alkyl group; or $R^{14}$ denotes a group

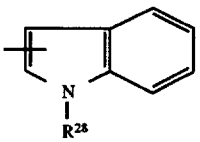

(where $R^{28}$ is a hydrogen atom or a $C_1$–$C_3$ alkyl group); or $R^{14}$ denotes a group represented by a group

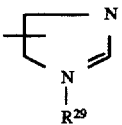

where $R^{29}$ is a hydrogen atom or a $C_1$–$C_3$ alkyl group); or $R^{14}$ denotes a thiazolyl group, and c stands for an integer of 1 to 3, or (v) a group represented by the formula

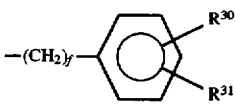

in which $R^{30}$ and $R^{31}$ denote a hydrogen atom, a hydroxyl group, a $C_1$–$C_3$ alkoxyl group or a halogen atom and f stands for an integer of 0 to 3, or (vi) a group represented by the formula

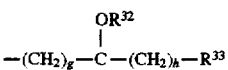

in which $R^{32}$ denotes a hydrogen atom, a $C_1$–$C_3$ alkyl group, a group represented by

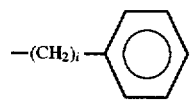

(where i is an integer of 0 to 3) or a group represented by —$COR^{34}$ (where $R^{34}$ is a hydrogen atom, methyl group or ethyl group); and $R^{33}$ denotes a hydrogen atom, a phenyl group or a group represented by

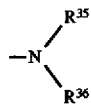

(where $R^{35}$ and $R^{36}$ independently are a hydrogen atom or a $C_1$–$C_3$ alkyl group); g stands for an integer of 0 to 3, and h stands for an integer of 0 to 2, or (vii) a group represented by the formula

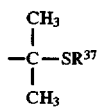

in which $R^{37}$ denotes a hydrogen atom or a $C_1$–$C_3$ alkyl group;

or $R^3$ represents (viii) a $C_1$–$C_8$ alkyl group having one to three hydroxyl group(s) as substituents on the non-terminal carbon atom(s) present in the chain of said $C_1$–$C_8$ alkyl group; or $R^2$ and $R^3$ may be coupled to each other as taken with the nitrogen atom to which $R^2$ is attached and also with the carbon atom to which $R^3$ is attached, to form a ring of the formula

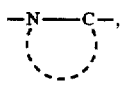

said ring

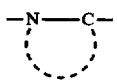

being selected from the group consisting of a cyclic radical having a cyclic structure

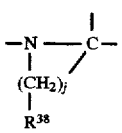

[in which $R^{38}$ is a hydrogen atom, a group represented by

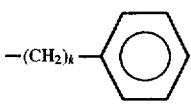

(k: an integer of 0 to 3) or a group represented by —$COR^{40}$ (where $R^{40}$ is a hydrogen atom, methyl or ethyl group), and j stands for an integer of 2 to 4| and a cyclic radical having a cyclic structure

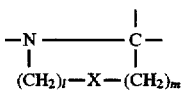

[in which X is an oxygen atom, a sulfur atom or a group —$NR^{41}$ (where $R^{41}$ is a hydrogen atom or a $C_1$–$C_3$ alkyl group), 1 stands for an integer of 1 to 3, and m stands for an integer of 0 to 2];

$R^4$ represents a hydrogen atom, a $C_1$–$C_3$ alkyl group or a group represented by

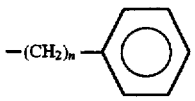

where n stands for an integer of 0 to 2; or $R^3$ and $R^4$ may be coupled to each other to form a chain of methylene group(s), so that $R^3$ and $R^4$, as taken together with the carbon atom to which $R^3$ and $R^4$ are attached, may form a cyclic group

(where p is an integer of 2 to 5); and $R^5$ represents a group represented by the formula —$OR^{42}$ in which $R^{42}$ denotes a hydrogen atom, a $C_1$–$C_3$ alkyl group or a group

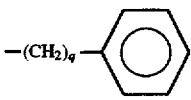

(q: an integer of 0–2), or $R^5$ represents a group represented by the formula

in which $R^{43}$ and $R^{44}$ denote a hydrogen atom or a $C_1$–$C^3$ alkyl group;

with the proviso that $R^1$ is not such a $C_5$ alkyl group as substituted by two of a group of the formula —$OR^6$, when y is zero and when $R^3$ is represented by a group —$(CH_2)_c$—$R^{14}$ where $R^{14}$ is —$OR^{15}$ and c is 1 and when $R^4$ is a methyl group;

or a salt of said amino acid derivative.

The novel amino acid derivative of the general formula (I) can form a salt with a base when the amino acid derivative is a compound belonging to the following cases. Namely, the novel amino acid derivative of the general formula (I) according to the present invention can form a salt with a base when the amino acid derivative is of the general formula (I) in which $R^1$ is a $C_1$–$C_8$ alkyl group substituted by —$COR^{12}$ where $R^{12}$ is OH group; in which $R^3$ is represented by —$(CH_2)_c$—$R^{14}$ where $R^{14}$ is represented by —$SO_2R^{18}$, with $R^{18}$ being OH group; in which $R^3$ is also represented by —$(CH_2)_c$—$R^{14}$ where $R^{14}$ is represented by —$COR^{22}$ with $R^{22}$ being OH group; in which $R^3$ is represented by

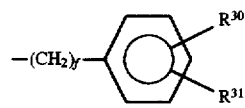

but at least one of $R^{30}$ and $R^{31}$ being OH group; or in which $R^5$ is represented by —$OR^{42}$ with $R^{42}$ being a hydrogen atom.

Further, the novel amino acid derivative of the general formula (I) can form a salt with an acid when the amino acid derivative is a compound belonging to the following cases. Namely, the novel amino acid derivative of the general formula (I) according to the present invention can form a salt with an acid when the amino acid derivative is of the general formula (I) in which $R^1$ is an alkyl group substituted by substituent(s)

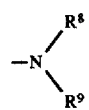

where $R^8$ and $R^9$ are individually a hydrogen atom or an alkyl group; in which $R^3$ is represented by —$(CH_2)_c$—$R^{14}$ where $R^{14}$ is

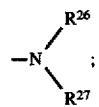

in which $R^3$ is represented by —$(CH_2)_c$—$R^{14}$ where $R^{14}$ is

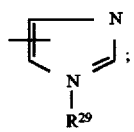

in which $R^3$ is —$(CH_2)_c$—$R^{14}$ where $R^{14}$ is a thiazolyl group; in which $R^3$ is

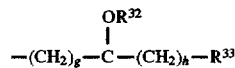

where $R^{33}$ is

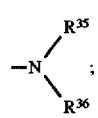

or in which $R^2$ and $R^3$ are coupled together to form a ring

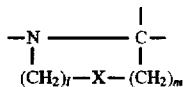

where X is $-NR^{41}$.

Illustrative salts of the novel amino acid derivative according to the present invention include the following salts: (1) salts with metals such as alkali metals, alkaline earth metals and aluminum; (2) ammonium salt; (3) salts with organic bases such as methylamine, ethylamine, diethylamine, triethylamine, pyrrolidine, piperidine, morpholine, hexamethyleneimine, aniline and pyridine; (4) salts with organic acids such as formic acid, acetic acid, trichloroacetic acid, maleic acid, tartaric acid, methanesulfonic acid, benzenesulfonic acid and toluenesulfonic acid; (5) salts with inorganic acids such as hydrochloric acid, hydrobromic acid, sulfuric acid and phosphoric acid; and (6) salts with amino acids such as arginine, glutamic acid and ornithine. When it is desired to use such salts as immunomodulators, antitumor agents or hematopoietic stem cell amplifiers, it is possible to select pharmacologically acceptable salts of the amino acid derivative of the general formula (I).

Compounds which are representative examples of the novel amino acid derivative of the general formula (I) according to the present invention are presented in the following Table 1a to Table 1b. Further, elemental analysis data of each of these illustrative compounds shown in Table 1a to Table 1b are mentioned in Table 2a to Table 2b below, and proton nuclear magnetic resonance absorption spectrum ($^1$H-NMR) data of each of these compounds are described in Table 3a to Table 3b below. The compound numbers shown in Table 1a to Table 1b are referred to in Tests and Experiments which will be described hereinafter.

TABLE 1a

| Compound No. | $R^1$ | $R^2$ | $R^3$ | $R^4$ | $R^5$ | y | Empirical formula (m.p.) |
|---|---|---|---|---|---|---|---|
| 1 | CH$_3$CH$_2$CHCH$_2$—<br>           \|<br>           CH$_3$ | H | HOCH$_2$— | CH$_3$— | HO— | 0 | C$_{10}$H$_{19}$O$_4$N |
| 2 | CH$_3$CH$_2$CHCH$_2$—<br>           \|<br>           CH$_3$ | H | HOCH$_2$— | CH$_3$— | C$_6$H$_5$—CH$_2$O— | 0 | C$_{17}$H$_{25}$O$_4$N |
| 3 | CH$_3$CHCH$_2$CH$_2$—<br>    \|<br>    OH | H | HOCH$_2$— | CH$_3$— | HO— | 0 | C$_9$H$_{17}$O$_5$N |
| 4 | CH$_3$CHCH$_2$CH$_2$—<br>    \|<br>    OH | H | HOCH$_2$— | CH$_3$— | CH$_3$(CH$_2$)$_3$O— | 0 | C$_{13}$H$_{25}$O$_5$N |
| 5 | CH$_3$CHCH$_2$—<br>    \|<br>    OH | H | HOCH$_2$— | CH$_3$— | HO— | 0 | C$_8$H$_{15}$O$_5$N |
| 6 | CH$_3$CHCH$_2$—<br>    \|<br>    OH | H | C$_6$H$_5$—CH$_2$OCH$_2$— | CH$_3$— | C$_6$H$_5$—CH$_2$O— | 0 | C$_{22}$H$_{27}$O$_5$N |
| 7 | CH$_3$CH—CH—<br>   \|   \|<br>   CH$_3$ OH | H | HOCH$_2$— | CH$_3$— | HO— | 0 | C$_9$H$_{17}$O$_5$N |
| 8 | CH$_3$CH—CH—<br>   \|   \|<br>   CH$_3$ OH | H | HOCH$_2$— | CH$_3$— | C$_6$H$_5$—CH$_2$O— | 0 | C$_{16}$H$_{23}$O$_5$N |
| 9 | CH$_3$CH—CH—CH—<br>   \|   \|   \|<br>   OH CH$_3$ OH | H | CH$_3$CHCH$_2$—<br>    \|<br>    CH$_3$ | H | HO— | 0 | C$_{12}$H$_{23}$O$_5$N |
| 10 | CH$_3$CHCH—CH—<br> \|   \|   \|<br> HO CH$_3$ OH | H | CH$_3$CHCH$_2$—<br>    \|<br>    CH$_3$ | H | C$_6$H$_5$—CH$_2$O— | 0 | C$_{19}$H$_{27}$O$_5$N (98–99° C.) |
| 11 | CH$_3$CHCH—CH—<br> \|   \|   \|<br> HO CH$_3$ OH | H | HOCH$_2$— | H | HO— | 0 | C$_9$H$_{17}$O$_6$N |

TABLE 1a-continued

| Compound No. | R¹ | R² | R³ | R⁴ | R⁵ | y | Empirical formula (m.p.) |
|---|---|---|---|---|---|---|---|
| 12 | CH$_3$CHCH—CH—<br>   \|    \|    \|<br>  HO  CH$_3$  OH | H | HOCH$_2$— | H | [phenyl]—CH$_2$O— | 0 | C$_{16}$H$_{23}$O$_6$N<br>(86–89° C.) |
| 13 | H$_3$C  OH<br>     \|    \|<br>HOCH$_2$—C—CH—<br>     \|<br>     CH$_3$ | H | HOCH$_2$— | CH$_3$— | HO— | 0 | C$_{10}$H$_{19}$O$_6$N |
| 14 | H$_3$C  OH<br>     \|    \|<br>HOCH$_2$—C—CH—<br>     \|<br>     CH$_3$ | H | HOCH$_2$— | CH$_3$— | CH$_3$O— | 0 | C$_{11}$H$_{21}$O$_6$N |
| 15 | H$_3$C  OH<br>     \|    \|<br>HOCH$_2$—C—CH—<br>     \|<br>     CH$_3$ | H | HOCH$_2$— | CH$_3$— | [phenyl]—CH$_2$O— | 0 | C$_{11}$H$_{25}$O$_6$N |
| 16 | CH$_3$CHCH—CH—CH—<br>   \|    \|    \|    \|<br>  H$_3$C OH CH$_3$ OH | H | HOCH$_2$— | CH$_3$— | HO— | 0 | C$_{12}$H$_{23}$O$_6$N |
| 17 | CH$_3$CHCH—CH—CH—<br>   \|    \|    \|    \|<br>  H$_3$C OH CH$_3$ OH | H | HOCH$_2$— | CH$_3$— | [phenyl]—CH$_2$O— | 0 | C$_{19}$H$_{29}$O$_6$N |
| 18 | CH$_3$CH—CH—CH—<br>   \|    \|    \|<br>  HO  CH$_3$  OH | H | CH$_3$SCH$_2$— | H | CH$_3$O— | 0 | C$_{11}$H$_{21}$O$_5$SN |
| 19 | CH$_3$CH—CH—CH—<br>   \|    \|    \|<br>  HO  CH$_3$  OH | H | CH$_3$SCH$_2$— | H | [phenyl]—CH$_2$O— | 0 | C$_{17}$H$_{25}$O$_5$SN<br>(78–81° C.) |
| 20 | CH$_3$CH—CH—CH—<br>   \|    \|    \|<br>  HO  CH$_3$  OH | H | [phenyl]—CH$_2$SCH$_2$— | H | [phenyl]—CH$_2$O— | 0 | C$_{23}$H$_{29}$O$_5$SN<br>(78–79° C.) |

TABLE 1b

| Compound No. | R¹ | R² | R³ | R⁴ | R⁵ | y | Empirical formula (m.p.) |
|---|---|---|---|---|---|---|---|
| 21 | CH$_3$CHCH—CH—<br>   \|    \|    \|<br>  HO  CH$_3$  OH | H | CH$_3$CH—<br>    \|<br>    OH | H | [phenyl]—CH$_2$O— | 0 | C$_{17}$H$_{25}$NO$_6$<br>(Oil) |
| 22 | CH$_3$CHCH—CH—<br>   \|    \|    \|<br>  HO  CH$_3$  OH | H | CH$_3$— | H | [phenyl]—CH$_2$O— | 0 | C$_{16}$H$_{23}$NO$_5$<br>(Oil) |
| 23 | CH$_3$CHCH—CH—<br>   \|    \|    \|<br>  HO  CH$_3$  OH | H | CH$_3$CH—<br>    \|<br>    OH | H | HO— | 0 | C$_{10}$H$_{19}$NO$_6$<br>(decomposed at 159–160° C.) |
| 24 | CH$_3$CHCH—CH—<br>   \|    \|    \|<br>  HO  CH$_3$  OH | H | CH$_3$— | H | HO— | 0 | C$_9$H$_{17}$NO$_5$<br>(decomposed at 281–282° C.) |

TABLE 1b-continued

| Compound No. | R¹ | R² | R³ | R⁴ | R⁵ | y | Empirical formula (m.p.) |
|---|---|---|---|---|---|---|---|
| 25 | CH₃CHCH—CH—<br>  \|   \|   \|<br>  HO  CH₃  OH | H | CH₃— | CH₃— | ⌬—CH₂O— | 0 | C₁₇H₂₅NO₅ (Oil) |
| 26 | CH₃CHCH—CH—<br>  \|   \|   \|<br>  HO  CH₃  OH | H | CH₃— | CH₃— | HO— | 0 | C₁₀H₁₉NO₅ (Oil) |
| 27 | HOCH₂CH₂CH—<br>        \|<br>        NH₂ | H | HOCH₂— | CH₃— | HO— | 0 | C₈H₁₆N₂O₅ (Oil) |
| 28 | CH₃CHCH—CH—<br>  \|   \|   \|<br>  HO  CH₃  OH | H | CH₃— | H | ⌬—CH₂O— | 1 | C₁₇H₂₅NO₅ (Oil) |
| 29 | CH₃CH—CH—CH—<br>  \|   \|   \|<br>  HO  CH₃  OH | H | CH₃— | H | HO— | 1 | C₁₀H₁₉NO₅ (decomposed at 167–168° C.) |

TABLE 2a

| | Elemental Analysis | | | | | |
|---|---|---|---|---|---|---|
| | C | | H | | N | |
| Compound No. | Found value | Theoretical value | Found value | Theoretical value | Found value | Theoretical value |
| 1 | 55.61 | 55.28 | 9.08 | 8.82 | 6.10 | 6.45 |
| 2 | 66.17 | 66.42 | 8.32 | 8.20 | 4.25 | 4.56 |
| 3 | 49.64 | 49.30 | 8.14 | 7.82 | 6.70 | 6.39 |
| 4 | 56.41 | 56.70 | 9.37 | 9.15 | 4.73 | 5.09 |
| 5 | 46.57 | 46.82 | 7.14 | 7.37 | 7.16 | 6.83 |
| 6 | 68.21 | 68.55 | 7.27 | 7.06 | 3.25 | 3.63 |
| 7 | 48.98 | 49.30 | 7.63 | 7.82 | 6.02 | 6.39 |
| 8 | 62.43 | 62.12 | 7.35 | 7.49 | 4.88 | 4.53 |
| 9 | 54.81 | 55.15 | 9.04 | 8.87 | 5.63 | 5.36 |
| 10 | 64.59 | 64.93 | 8.67 | 8.32 | 4.30 | 3.99 |
| 11 | 46.28 | 45.95 | 7.44 | 7.28 | 5.61 | 5.96 |
| 12 | 58.72 | 59.06 | 6.97 | 7.13 | 4.00 | 4.31 |
| 13 | 48.41 | 48.18 | 7.83 | 7.68 | 5.39 | 5.62 |
| 14 | 50.39 | 50.18 | 7.85 | 8.04 | 5.06 | 5.32 |
| 15 | 60.48 | 60.16 | 7.24 | 7.43 | 4.48 | 4.13 |
| 16 | 52.29 | 51.97 | 8.66 | 8.36 | 4.79 | 5.05 |
| 17 | 62.44 | 62.10 | 8.04 | 7.96 | 3.52 | 3.81 |
| 18 | 47.01 | 47.30 | 7.36 | 7.58 | 5.23 | 5.01 |
| 19 | 57.27 | 57.45 | 7.18 | 7.09 | 4.26 | 3.94 |
| 20 | 63.63 | 64.02 | 6.91 | 6.77 | 2.90 | 3.25 |

TABLE 2b

| | Elemental Analysis | | | | | |
|---|---|---|---|---|---|---|
| | C | | H | | N | |
| Compound No. | Found value | Theoretical value | Found value | Theoretical value | Found value | Theoretical value |
| 21 | 60.54 | 60.16 | 7.57 | 7.43 | 4.44 | 4.13 |
| 22 | 62.46 | 62.12 | 7.74 | 7.49 | 4.29 | 4.53 |
| 23 | 48.29 | 48.18 | 7.72 | 7.68 | 5.65 | 5.62 |
| 24 | 49.18 | 49.30 | 7.65 | 7.82 | 6.28 | 6.39 |
| 25 | 63.45 | 63.14 | 7.97 | 7.79 | 4.41 | 4.33 |
| 26 | 51.77 | 51.49 | 8.50 | 8.21 | 6.00 | 6.01 |

TABLE 2b-continued

| | Elemental Analysis | | | | | |
|---|---|---|---|---|---|---|
| | C | | H | | N | |
| Compound No. | Found value | Theoretical value | Found value | Theoretical value | Found value | Theoretical value |
| 27 | 43.88 | 43.63 | 7.59 | 7.32 | 12.77 | 12.72 |
| 28 | 63.48 | 63.14 | 7.90 | 7.79 | 4.51 | 4.33 |
| 29 | 51.16 | 51.49 | 8.27 | 8.21 | 6.03 | 6.01 |

TABLE 3a

| Compound No. | ¹H-NMR(δ)(ppm) |
|---|---|
| 1 | (CDCl₃); 0.87(t, J=7Hz, 3H), 0.90(d, J=7Hz, 3H), 1.19(m, 1H), 1.35(m, 1H), 1.50(s, 3H), 1.80–2.30(m, 3H), 3.70–4.10(brd, 2H) |
| 2 | (CDCl₃); 0.87(t, J=7Hz, 3H), 0.92(d, J=7Hz, 3H), 1.10–1.45 (m, 2H), 1.53(s, 3H), 1.60–2.33(m, 3H), 3.80, 4.07(AB system, J=12Hz, 2H), 5.17(s, 2H), 7.33(s, 5H) |
| 3 | (CDCl₃); 1.18(d, J=6Hz, 3H), 1.47(s, 3H), 1.75(td, J=6Hz, 2H), 2.37(t, J=7Hz, 2H), 3.82(qt, J=6.6Hz, 1H), 3.87(brs, 2H) |
| 4 | (CDl₃); 0.98(t, J=7Hz, 3H), 1.23(d, J=6Hz, 3H), 1.25–2.06 (m, 6H), 1.53(s, 3H), 2.41(t, J=6Hz, 2H), 3.70–4.02(m, 1H), 3.90(brs, 2H), 4.22(t, J=6Hz, 2H) |
| 5 | (CD₃OD); 1.24(d, J=6Hz, 3H), 1.51(s, 3H), 2.36(d, J=6Hz, 2H), 3.66–4.32(m, 3H) |
| 6 | (CDCl₃); 1.16(d, J=6Hz, 3H), 1.57(s, 3H), 2.30(d, J=5Hz, 2H), 3.80(m, 2H), 4.11(m, 1H), 4.43(s, 2H), 5.14(s, 2H), 7.24(s, 5H), 7.30(s, 5H) |
| 7 | (CD₃OD); 0.92(d, J=7Hz, 3H), 1.05(d, J=7Hz, 3H), 1.57(s, 3H), 1.84–2.36(m, 1H), 3.85, 4.08(AB system, J=12Hz, 2H), 3.90 (d, J=4Hz, 1H) |
| 8 | (CDCl₃); 0.82(d, J=7Hz, 3H), 0.97(d, J=7Hz, 3H), 1.62(s, 3H), 1.70–2.21(m, 1H), 3.97(d, J=4Hz, 1H), 4.53, 4.92(AB system, J=12Hz, 2H), 5.20(d, J=2Hz, 2H), 7.37(s, 5H) |
| 9 | (CD₃OD); 0.93(d, J=6Hz, 3H), 0.97(d, J=4Hz, 6H), 1.23 (d, J=6Hz, 3H), 1.43–2.06(m, 4H), 3.91(qd, J=6.6Hz, 1H), 4.24 (d, J=3Hz, 1H), 4.47(m, 1H) |
| 10 | (CDCl₃); 0.84(d, J=6Hz, 3H), 0.93(d, J=5Hz, 6H), 1.18 (d, J=6Hz, 3H), 1.40–1.52(m, 3H), 1.85–2.15(m, 1H), 4.17(m, 1H), 4.32(d, J=2Hz, 1H), 4.47–4.80(m, 1H), |

TABLE 3a-continued

| Compound No. | $^1$H-NMR($\delta$)(ppm) |
|---|---|
| | 5.14(s, 2H), 7.33(s, 5H) |
| 11 | (CD$_3$OD); 0.93(d, J=6Hz, 3H), 1.23(d, J=6Hz, 3H), 1.67–2.12 (m, 1H), 3.84–4.10(m, 1H), 3.92(m, 2H), 4.23–4.50(m, 1H), 4.26(m, 1H) |
| 12 | (CDCl$_3$); 0.87(d, J=6Hz, 3H), 1.17(d, J=6Hz, 3H), 1.80–2.20 (m, 1H), 3.80–4.26(m, 1H), 3.96(m, 2H), 4.36(d, J=2Hz, 1H), 4.70(m, 1H), 5.16(s, 2H), 7.36(s, 5H) |
| 13 | (CD$_3$OD); 0.96(s, 3H), 1.03(s, 3H), 1.52(s, 3H), 3.44(s, 2H) 3.91(m, 3H) |
| 14 | (CDCl$_3$); 0.94(s, 3H), 1.03(s, 3H), 1.53(s, 3H), 3.47(s, 2H), 3.70–3.95(m, 3H), 3.78(s, 3H) |
| 15 | (CDCl$_3$); 0.92(s, 3H), 0.98(s, 3H), 1.54(s, 3H), 3.43(s, 2H), 3.92(s, 2H), 3.94(s, 1H), 5.20(s, 2H), 7.36(s, 5H) |
| 16 | (CD$_3$OD); 0.84(d, J=6Hz, 3H), 0.97(d, J=6Hz, 3H), 1.03 (d, J=6Hz, 3H), 1.33–1.90(m, 1H), 1.53(s, 3H), 1.96–2.40 (m, 1H), 2.33–3.56(m, 1H), 3.91(br s, 2H), 4.02(d, J=4Hz, 1H) |
| 17 | (CD$_3$OD); 0.81(d, J=7Hz, 3H), 0.94(d, J=7Hz, 3H), 0.97 (d, J=7Hz, 3H), 1.32–1.90(m, 1H), 1.53(s, 3H), 1.96–2.34(m, 1H), 3.30–3.73(m, 1H), 3.86(br s, 2H), 3.99(d, J=4Hz, 1H), 5.17(s, 2H), 7.36(s, 5H) |
| 18 | (CD$_3$OD); 0.89(d, J=6Hz, 3H), 1.21(d, J=6Hz, 3H), 1.80–2.20(m, 1H), 2.09(s, 3H), 2.99(d, J=5Hz, 2H), 3.87(s, 3H), 4.38(d, J=2Hz, 1H), 4.87(m, 1H) |
| 19 | (CDCl$_3$); 0.91(d, J=6Hz, 3H), 1.28(d, J=6Hz, 3H), 2.11(s, 3H), 3.01(d, J=5Hz, 2H), 4.24(m, 1H), 4.41(d, J=2Hz, 1H), 4.76–5.06 (m, 1H), 5.23(s, 2H), 7.40(s, 5H) |
| 20 | (CDCl$_3$); 0.86(d, J=6Hz, 3H), 1.19(d, J=6Hz, 3H), 2.02(m, 1H), 2.85(d, J=6Hz, 2H), 3.67(s, 2H), 4.15(m, 1H), 4.34(d, J=2Hz, 1H), 4.66–4.96(m, 1H), 5.13(s, 2H), 7.24(s, 5H), 7.32(s, 5H) |

TABLE 3b

| Compound No. | $^1$H-NMR($\delta$)(ppm) |
|---|---|
| 21 | (CDCl$_3$); 0.86(d, J=7Hz, 3H), 1.21(d, J=6Hz, 6H), 2.01–2.09 (m, 1H), 4.16–4.23(m, 1H), 4.35–4.42(m, 1H), 4.43(d, J=2Hz, 1H), 4.60–4.66(m, 1H), 5.20(dd, J=12, 12Hz, 2H), 7.35(s, 5H) |
| 22 | (CDCl$_3$); 0.88(d, J=7Hz, 3H), 1.22(d, J=6Hz, 3H), 1.45(d, J=7Hz, 3H), 2.00–2.10(m, 1H), 4.10–4.30(m, 1H), 4.36(s, 1H), 4.50–4.80(m, 1H), 5.18(dd, J=14, 12Hz, 2H), 7.35(s, 5H) |
| 23 | (CD$_3$OD); 0.98(d, J=7Hz, 3H), 1.23(d, J=6Hz, 3H), 1.25(d, J=6Hz, 3H), 1.78–2.12(m, 1H) 3.83–4.24(m, 2H), 4.33(d, J=2Hz, 1H), 4.42(s, 1H) |
| 24 | (CD$_3$OD); 0.98(d, J=7Hz, 3H), 1.23 (d, J=6Hz, 3H), 1.25(d, J=6Hz, 3H), 1.78–2.12(m, 1H), 3.83–4.24(m, 2H), 4.33(d, J=2Hz, 1H), 4.42(s, 1H) |
| 25 | (CDCl$_3$); 0.83(d, J=7Hz, 3H), 1.21(d, J=6Hz, 3H), 1.57(s, 3H), 1.59(s, 3H), 2.02(m,1H), 4.19(m, 1H), 4.27(d, J=2Hz, 1H), 5.17(s, 2H), 7.34(s, 5H) |
| 26 | (CD$_3$OD); 0.91(d, J=7Hz, 3H), 1.22(d, J=6Hz, 3H), 1.55(s, 3H), 1.56(s, 3H), 1.90(m, 1H), 3.89(m, 1H), 4.14(d, J=2Hz, 1H) |
| 27 | (CD$_3$OD); 1.45(s, 3H), 2.06(m, 2H), 3.34, 3.81(AB system, J=12Hz, 2H), 3.81(t, J=6Hz, 2H), 4.09(m, 1H) |
| 28 | (CDCl$_3$); 0.85(d, J=7Hz, 3H), 1.22(d, J=6Hz, 3H), 1.24 (d, 7Hz, 1H), 2.04(m, 1H), 2.59(m, 2H), 4.19(m, 1H), 4.27 (d, J=2Hz, 1H), 4.40 (m, ,1H), 5.13(s, 2H), 7.36(s, 5H) |
| 29 | (CD$_3$OD); 0.88(d, J=7Hz, 3H), 1.22(d, J=6Hz, 3H), 1.26(d, J=6Hz, 3H), 1.92(m, 1H), 2.50(m, 2H), 3.93(m, 1H), 4.19(d, J=1.5Hz, 1H), 4.32(m, 1H) |

Incidentally, the amino acid derivative of the general formula (I) according to the present invention embraces, as preferred embodiments thereof, five types of such amino acid derivatives represented by the following general formulae (I-1), (I-2), (I-3), (I-4) and (I-5), respectively:

(A) An amino acid derivative represented by the general formula:

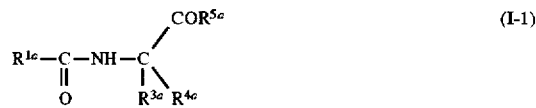

(I-1)

wherein $R^{1a}$ is a $C_1$–$C_8$ alkyl group or a $C_1$–$C_8$ alkyl group having one to two hydroxyl groups as substituents, $R^{3a}$ is a group represented by the formula —$(CH_2)_c$—$R^{14a}$ (where $R^{14a}$ is a hydroxyl group, a $C_1$–$C_3$ alkoxy group or an aralkyloxy group, e.g., benzyloxy or phenethyloxy group and c is an integer of 1, 2 or 3); or $R^{3a}$ is a $C_1$–$C_4$ alkyl group having one to three hydroxyl groups as substituents on the non-terminal carbon atom(s) in the chain of the alkyl group, $R^{4a}$ is a hydrogen atom or a $C_1$–$C_3$ alkyl group, and $R^{5a}$ is a hydroxyl group, a $C_1$–$C_3$ alkoxy group or an aralkyloxy group, for example, benzyloxy, phenethyloxy or phenoxy group;

(B) An amino acid derivative represented by the general formula:

(I-2)

wherein $R^{1a}$ is a $C_1$–$C_8$ alkyl group or a $C_1$–$C_8$ alkyl group having one to two hydroxyl groups as substituents, $R^{3b}$ is a $C_1$–$C_8$ alkyl group, $R^{4a}$ is a hydrogen atom or a $C_1$–$C_3$ alkyl group, and $R^{5a}$ is a hydroxyl group, a $C_1$–$C_3$ alkoxy group or an aralkyloxy group, for example, benzyloxy, phenethyloxy or phenoxy group;

(C) An amino acid derivative represented by the general formula:

(I-3)

wherein $R^{1a}$ is a $C_1$–$C_8$ alkyl group or a $C_1$–$C_8$ alkyl group having one to two hydroxyl groups as substituents, $R^{3c}$ is a group of the formula —$(CH_2)_c$—$R^{14b}$ (where $R^{14b}$ is thiol group (—SH), a $C_1$–$C_3$ alkylthio group or an aralkylthio group, e.g., benzylthio or phenethylthio group and c is an integer of 1, 2 or 3), $R^{4a}$ is a hydrogen atom or a $C_1$–$C_3$ alkyl group, and $R^{5a}$ is a hydroxyl group, a $C_1$–$C_3$ alkoxy group or an aralkyloxy group, for example, benzyloxy, phenethyloxy or phenoxy group;

(D) An amino acid derivative represented by the general formula:

(I-4)

wherein $R^{1a}$ is a $C_1$–$C_8$ alkyl group or a $C_1$–$C_8$ alkyl group having one to two hydroxyl groups as substituents, $R^{3d}$ is a $C_1$–$C_8$ alkyl group or a group of the formula —$(CH_2)_c$—$R^{14a}$ (where $R^{14a}$ is a hydroxyl group, a $C_1$–$C_3$ alkoxy group or an aralkyloxy group, e.g., benzyloxy or phenethyloxy group and c is an integer of 1, 2 or 3), $R^{4a}$ is a hydrogen atom or a $C_1$–$C_3$ alkyl group, and $R^{5a}$ is a hydroxyl group, a $C_1$–$C_3$ alkoxy group or an aralkyloxy group, for example, benzyloxy, phenethyloxy or phenoxy group; and (E) An amino acid derivative represented by the general formula:

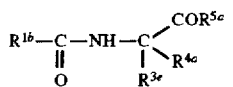  (I-5)

wherein $R^{1b}$ is a $C_1$–$C_8$ alkyl group having one to two hydroxyl groups and one to two amino groups as substituents, $R^{3e}$ is a group of the formula —(CH$_2$)$_c$—$R^{14a}$ (where $R^{14a}$ is a hydroxyl group, a $C_1$–$C_3$ alkoxy group or an aralkyloxy group, e.g., benzyloxy or phenethyloxy group and c is an integer of 1, 2 or 3), $R^{4a}$ is a hydrogen atom or a $C_1$–$C_3$ alkyl group, and $R^{5a}$ is a hydroxyl group, a $C_1$–$C_3$ alkoxy group or an aralkyloxy group, for example, benzyloxy, phenethyloxy or phenoxy group.

The group $R^1$ in the amino acid derivative of the general formula (I) and the group $R^{1a}$ in the amino acid derivatives of the general formulae (I-1) to (I-4) are preferably a linear or branched alkyl group or a mono- or di-hydroxy-substituted linear or branched alkyl group which is represented by the following formulae:

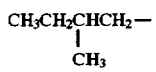 (i)

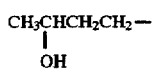 (ii)

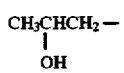 (iii)

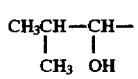 (iv)

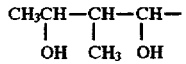 (v)

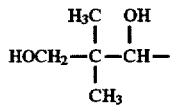 (vi)

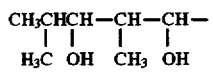 (vii)

$R^{1b}$ in the amino acid derivative of the general formula (I-5) is preferably a hydroxy- and amino-substituted alkyl group which is represented by the following formula:

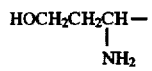 (viii)

The amino acid derivative of the general formula (I) according to the present invention is other than (2S)N-[(2R, 3S,4R)-2,4-dihydroxy-3-methylpentanoyl]-2-methylserine known under the name "conagenin" (see U.S. Pat. No. 5,098,935), because the meanings of $R^1$, $R^3$, $R^4$ and y are restricted by the "proviso" clause, as defined in the general formula (I).

BEST MODE FOR CARRYING OUT THE INVENTION

The novel amino acid derivative according to the present invention, which is represented by the formula (I), can be synthesized by several processes as will be described below.

According to one of such synthesis processes, the amino acid derivative of the general formula (I) can be synthesized by reacting a compound of the following general formula (II):

 (II)

wherein $R^1$ has the same meaning as defined above in the general formula (I) with an amine compound of the following general formula (III):

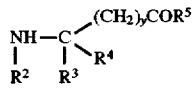 (III)

wherein $R^2$, $R^3$, $R^4$, $R^5$ and y have the same meanings as defined above in the general formula (I) in accordance with a usual reaction for amidating carboxylic acid compounds. This amidating reaction can be conducted, for example, in the absence of any catalyst, or in the presence of a dehydrating condensation agent or in the presence of a base. As said dehydrating condensation agent, a conventional dehydrating condensation agent can be used such as dicyclohexylcarbodiimide or 1-ethyl-3-(3-dimethylaminopropyl) carbodiimide. Illustrative examples of the base include a metal alcoholate such as sodium methoxide, an alkyl metal such as butyl lithium, and a metal hydride such as sodium hydride.

Also employable is such a process in which the carboxylic acid compound of the formula (II) is converted into an acid halide by a halogenating reagent such as phosphorus pentachloride or thionyl chloride, followed by the reaction of the acid halide with the amine compound of the formula (III). In this reaction, the synthetic reaction can occasionally be promoted by adding 1-hydroxybenzotriazole, N-hydroxysuccinimide or the like in some instances. For said reaction with the amine compound of the formula (III), an ester of the following formula (IV):

 (IV)

wherein $R^{45}$ represents an alkyl group, a phenyl group or a substituted phenyl group and $R^1$ has the same meaning as defined above can be used in place of the carboxylic acid compound of the formula (II). As an alternative, where the carboxylic acid compound of the formula (II) contains a hydroxyl-substituted alkyl group as $R^1$ and can form a lactone ring between the hydroxyl group and the carboxyl group, it is possible to use a lactone compound for said carboxylic acid derivative. For instance, when a carboxylic acid compound of the general formula (II) used is such a carboxylic acid containing a group of the following formula (V):

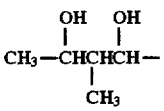 (V)

as $R^1$, the reaction of a lactone of the following formula (VI):

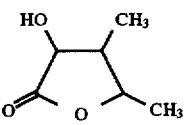 (VI)

namely, 2-hydroxy-3,4-dimethyl-γ-butyrolactone (see Example 5 given hereinafter) with the amine compound of the formula (III) may be conducted in the presence of an inorganic catalyst or a base. In this reaction, the base usable includes metal alcoholates such as sodium methoxide, an alkyl metal such as butyl lithium, and metal hydrides such as sodium hydride.

Further, usable is such a process in which, similarly to the case with making use of the carboxylic acid compound of the formula (II), an ester compound of the aforesaid formula (IV) or a lactone compound such as that of the formula (VI) is converted into an acid halide by a halogenating reagent e.g. phosphorus pentachloride or thionyl chloride, followed by reaction of the acid halide with the amine compound of the formula (III). For conducting each of these reactions, if necessary, it is possible to introduce beforehand the conventional protecting group(s) into the compound(s) to be used in the reaction, and after the reaction, to remove the protecting group(s) from the reaction product so obtained. In the carboxylic acid compound of the formula (II) or the amine compound of the formula (III) to be used, for example, it is possible to protect a hydroxyl group of said compound by tetrahydropyranyl group, trimethylsilyl group or the like, to protect an amino group of said compound by acetyl group, carboxybenzyl group, t-butoxycarbonyl group or the like, to protect a mercapto group of said compound by acetyl group, t-butoxycarbonyl group or the like, and to protect a carboxyl group of said compound by benzyl group, methyl group or the like.

In order to synthesize such an amino acid derivative of the formula (I) which contains an $OR^6$-substituted alkyl group as $R^1$ where $R^6$ is a $C_1$-$C_3$ alkyl group or a group

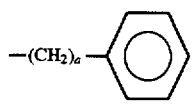

(a is as defined above), there can be used a process comprising a general etherifying reaction, including, for instance, such a process in which a compound of the formula (I) where $R^6$ is a hydrogen atom, namely, an amino acid derivative of the formula (I) containing a hydroxyl-substituted $C_1$-$C_8$ alkyl group as $R^1$ is reacted with a halide compound of the formula $R^{46}X^1$ where $R^{46}$ is a $C_1$-$C_3$ alkyl group or

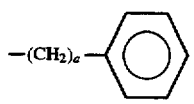

and $X^1$ is a halogen atom, in the presence of a base.

In order to synthesize such an amino acid derivative of the formula (I) in which $R^1$ is an $OR^6$-substituted $C_1$-$C_8$ alkyl group where $R^6$ is an acyl group —$COR^7$ ($R^7$ is as defined above), there can be used a process comprising a general esterifying reaction, including, for instance, such a process in which a corresponding amino acid derivative of the formula (I) where $R^6$ is a hydrogen atom is reacted with an organic acid anhydride of the formula $(R^7CO)_2O$ ($R^7$ is as defined above) in the presence of an acid such as sulfuric acid or p-toluenesulfonic acid or a base such as pyridine or lutidine; or such a process in which the amino acid derivative of the formula (I) where $R^6$ is a hydrogen atom is reacted with an acid halide of the formula $R^7COX^2$ ($R^7$ is as defined above and $X^2$ is a halogen atom) in the presence of an inorganic base such as an alkali metal hydroxide, e.g., sodium hydroxide or an organic base such as pyridine or triethylamine.

To synthesize such an amino acid derivative of the formula (I) in which $R^1$ is an alkyl group substituted by a group

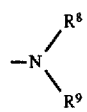

where $R^8$ and $R^9$ are each a $C_1$-$C_3$ alkyl group, a process comprising a general reaction for alkylating amines can be used, including such a process in which a compound of the formula (I) where $R^1$ is an alkyl group substituted by the group —$NR^8R^9$ ($R^8$ and $R^9$ are each a hydrogen atom) is reacted with an alkyl halide of the formula $R^{47}X^3$ ($R^{47}$ is a $C_1$-$C_3$ alkyl group and $X^3$ is a halogen atom).

To synthesize such an amino acid derivative of the formula (I) mentioned just in the above case, in which $R^1$ is an $NR^8R^9$-substituted alkyl group where $R^8$ is an acyl group —$COR^{10}$ ($R^{10}$ is as defined above), a process comprising a general reaction for acylating an amino group can be used, including such a process in which a corresponding amino acid compound of the formula (I) where $R^8$ is a hydrogen atom is acylated with an organic acid anhydride $(R^{10}CO)_2O$ ($R^{10}$ is as defined above) in the presence of an acid or a base, or such a process in which the amino acid compound (I) where $R^8$ is a hydrogen atom is reacted with an ester compound of the formula $R^{10}CO_2R^{48}$ ($R^{10}$ is H, methyl or ethyl group and $R^{48}$ is a $C_1$-$C_4$ alkyl group) in the presence of a base.

To synthesize such an amino acid derivative of the formula (I) in which $R^1$ is an $SR^{11}$-substituted alkyl group where $R^{11}$ is a $C_1$-$C_3$ alkyl group, a process comprising a general reaction for alkylating thiols can be used, including such a process in which a corresponding compound of the formula (I) where $R^{11}$ is a hydrogen atom is reacted with an alkyl halide of the formula $R^{49}X^5$ ($R^{49}$ is a $C_1$-$C_3$ alkyl group and $X^5$ is a halogen atom).

To synthesize such an amino acid derivative of the formula (I) in which $R^1$ is a $COR^{12}$-substituted alkyl group where $R^{12}$ is a group —$OR^{13}$ ($R^{13}$ is as defined above), a process comprising a general esterifying reaction can be used, including such a process in which a corresponding carboxylic acid of the formula (I) where $R^{12}$ is OH group is reacted with an alcohol of the formula $R^{13}OH$ ($R^{13}$ is as defined above) in the presence of an acid or a base, or such a process in which a corresponding carboxylic acid compound (I) where $R^{12}$ is OH group is converted into an acid halide by a usual halogenating reagent e.g., thionyl chloride or phosphorus pentachloride, followed by reaction of the acid halide with an alcohol of the formula $R^{13}OH$.

To synthesize such an amino acid derivative of the formula (I) in which $R^1$ is an

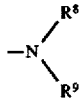

-substituted alkyl group ($R^8$ and $R^9$ are as defined above) or an —$SR^{11}$-substituted alkyl group ($R^{11}$ is as defined above), it is possible to use, for example, a process in which a corresponding amino acid compound of the formula (I) where $R^6$ is a hydrogen atom is sulfonylated with a sulfonylating agent such as tosyl chloride or methyl chloride or is halogenated with a halogenating reagent such as thionyl chloride, phosphorus pentachloride or phosphorus tribromide, followed by the reaction of the resultant sulfonate or halide with an alcohol of the formula $HOR^{46}$ ($R^{46}$ is as defined above), or an amine of the formula

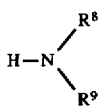

($R^8$ and $R^9$ are as defined above) or a thiol of the formula $HSR^{11}$ ($R^{11}$ is as defined above) in the presence of a base.

To synthesize such an amino acid derivative of the formula (I) in which $R^1$ is a $COR^{12}$-substituted alkyl group ($R^{12}$ is as defined above), a process comprising a general carboxylating reaction can be used, including such a process in which a corresponding compound of the formula (I) where $R^6$ is a hydrogen atom is similarly sulfonylated with a sulfonylating agent such as tosyl chloride or mesyl chloride or is halogenated with a halogenating agent and the resulting sulfonate or halide is then cyanated by reaction with a cyano compound of the formula $X^6CN$ ($X^6$ is sodium or potassium), followed by hydrolysis or alcoholysis of the resulting cyanation product.

To synthesize such an amino acid derivative of the formula (I) in which $R^3$ is a group —$(CH_2)_c$—$R^{14}$, where $R^{14}$ is —$OR^{15}$ and $R^{15}$ is a $C_1$–$C_3$ alkyl group or a group

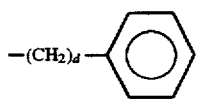

(d is as defined above), there can be used a process comprising a general etherifying reaction, including such a process in which a corresponding amino acid compound of the formula (I) where $R^{15}$ is a hydrogen atom is reacted with a halide compound of the formula $R^{50}X^7$ ($R^{50}$ is a $C_1$–$C_3$ alkyl group or a group

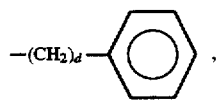

and $X^7$ is a halogen atom) in the presence of a base. To synthesize such an amino acid derivative of the formula (I) shown just above but where $R^{15}$ is an acyl group, —$COR^{16}$ ($R^{16}$ is as defined above), there can be used a process comprising a general esterifying reaction, including such a process in which a corresponding amino acid compound of the formula (I) where $R^{15}$ is a hydrogen atom is reacted with an organic acid anhydride of the formula ($R^{16}CO)_2O$ ($R^{16}$ is as defined above) in the presence of an acid or a base, or such a process in which a corresponding amino acid compound of the formula (I) where $R^{15}$ is a hydrogen atom is reacted with an acid halide of the formula $R^{16}COX^8$ ($R^{16}$ is as defined above and $X^8$ is a halogen atom) in the presence of a base.

Further, in order to synthesize such an amino acid derivative of the formula (I) in which $R^3$ is a group represented by —$(CH_2)_c$—$R^{14}$ where $R^{14}$ is a substituent —$SR^{17}$ ($R^{17}$ is as defined above) or a substituent

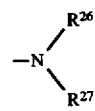

($R^{26}$ and $R^{27}$ are as defined above), it is possible to use, for example, such a process in which a corresponding amino acid compound of the formula (I) where $R^{14}$ is a hydroxyl group is sulfonylated with a sulfonylating agent such as tosyl chloride or mesyl chloride or is halogenated with a halogenating reagent such as thionyl chloride, phosphorus pentachloride or phosphorus tribromide, followed by the reaction of the resulting sulfonate or halide with a thiol of the formula $HSR^{17}$ ($R^{17}$ is as defined above) or with an amine of the formula

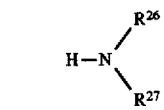

($R^{26}$ and $R^{27}$ are as defined above) in the presence of a base.

To synthesize such an amino acid derivative of the formula (I) in which $R^3$ is a group represented by —$(CH_2)_c$—$R^{14}$ where $R^{14}$ is a group —$COR^{22}$ and $R^{22}$ is a group —$OR^{23}$ ($R^{23}$ is as defined above), there can be used a process comprising a general carboxylating reaction, including such a process in which a corresponding amino acid compound of the formula (I) where $R^{14}$ is a hydroxyl group is similarly sulfonylated with a sulfonylating agent such as tosyl chloride or mesyl chloride or is halogenated with a halogenating reagent such as thionyl chloride, phosphorus pentachloride or phosphorus tribromide, and the resulting product is then cyanated by reaction with a cyano compound of the formula $X^9CN$ ($X^9$ is sodium or potassium), followed by hydrolysis or alcoholysis of the resulting cyanation product.

To synthesize such an amino acid derivative of the formula (I) in which $R^{22}$ is a group represented by

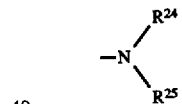

($R^{24}$ and $R^{25}$ are as defined above), there can be used a process comprising a general amidating reaction, including such a process in which a corresponding compound of the formula (I) where $R^{22}$ is a group —$OR^{23}$ ($R^{23}$ is as defined above) is either directly reacted with an amine

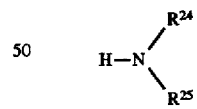

or reacted with a halogenating agent such as phosphorus pentachloride or thionyl chloride to form an acid halide derivative where $R^{14}$ is a group —$COX^{10}$ ($X^{10}$ is a halogen atom) and the latter halide is then reacted with an amine

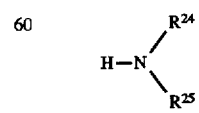

($R^{24}$ and $R^{25}$ are as defined above). To synthesize an amino acid derivative (I) in which $R^{14}$ is a group

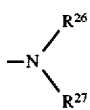

where $R^{26}$ and $R^{27}$ are each a $C_1$–$C_3$ alkyl group, there can be used a process comprising a general reaction for alkylating amines, including such a process in which a corresponding amino acid compound (I) where $R^{26}$ and $R^{27}$ are each a hydrogen atom is reacted with an alkyl halide of the formula $R^{51}X^{11}$ ($R^{51}$ is a $C_1$–$C_3$ alkyl group and $X^{11}$ is a halogen atom).

In order to synthesize such an amino acid derivative of the formula (I) in which $R^2$ is a group represented by

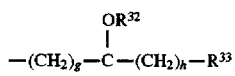

where $R^{32}$ is a $C_1$–$C_3$ alkyl group or a group

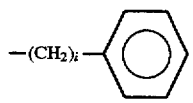

(i is as defined above), there can be used a process comprising a general etherifying reaction, including such a process in which a corresponding compound of the formula (I) where $R^{32}$ is a hydrogen atom is reacted with a halide compound of the formula $R^{52}X^{12}$ ($R^{52}$ is a $C_1$–$C_3$ alkyl group or a group

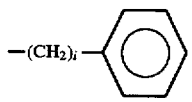

and $X^{12}$ is a halogen atom) in the presence of a base. To synthesize such an amino acid derivative of the formula (I) in which $R^{32}$ is a group represented by $COR^{34}$, there can be used a process comprising a general reaction for acylating a hydroxyl group, including such a process in which a corresponding amino acid compound of the formula (I) where $R^{32}$ is a hydrogen atom is acylated with an organic acid anhydride of the formula $(R^{34}CO)_2O$ ($R^{34}$ is as defined above) in the presence of an acid or a base, or such a process in which the corresponding compound (I) where $R^{32}$ is a hydrogen atom is acylated with an acid halide of the formula $R^{34}COX^{13}$ ($R^{34}$ is as defined above and $X^{13}$ is a halogen atom) in the presence of a base.

To synthesize such an amino acid derivative of the formula (I) mentioned just in the above case but in which $R^{33}$ is a group

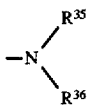

where $R^{35}$ and $R^{36}$ are each a $C_1$–$C_3$ alkyl group, there can be used a process comprising a general reaction for alkylating amines, including, for example, such a process in which a corresponding amino acid compound of the formula (I) where $R^{35}$ and $R^{36}$ are each a hydrogen atom is reacted with an alkyl halide of the formula $R^{53}X^{14}$ ($R^{53}$ is a $C_1$–$C_3$ alkyl group and $X^{14}$ is a halogen atom).

Further, in order to synthesize such an amino acid derivative of the formula (I) in which $R^2$ and $R^3$ are coupled together to form

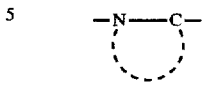

so as to represent a cyclic group

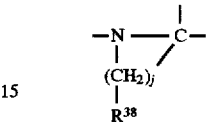

where $R^{38}$ is —$OR^{39}$ and $R^{39}$ is a $C_1$–$C_3$ alkyl group or a group

(k is as defined above), there can be used a process comprising a general etherifying reaction, including, for example, such a process in which a corresponding amino acid compound of the formula (I) where $R^{39}$ is a hydrogen atom is reacted with a halide compound of the formula $R^{54}X^{15}$ ($R^{54}$ is a $C_1$–$C_3$ alkyl group or a group

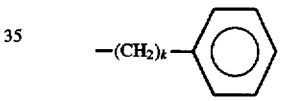

and $X^{15}$ is a halogen atom) in the presence of a base. Here, to synthesize the amino acid derivative of the formula (I) in which $R^{39}$ is a group —$COR^{43}$ ($R^{43}$ is as defined above), there can be used a process comprising a general reaction for acylation of hydroxyl group, including, for example, such a process in which a corresponding compound of the formula (I) where $R^{39}$ is a hydrogen atom is acylated with an organic acid anhydride of formula $(R^{40}CO)_2O$ in the presence of an acid or a base, or such a process in which a corresponding compound (I) where $R^{39}$ is a hydrogen atom is reacted with an acid halide of the formula $R^{40}COX^{16}$ ($R^{40}$ is as defined above and $X^{16}$ is a halogen atom) in the presence of a base.

Next, in order to synthesize such an amino acid derivative of the formula (I) in which $R^5$ is a group —$OR^{42}$ where $R^{42}$ is a $C_1$–$C_3$ alkyl group or is a group

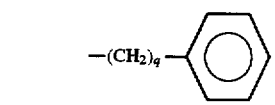

(q is as defined above), it is possible to use a process comprising a general esterifying reaction, including, for example, such a process in which a corresponding amino acid compound of the formula (I) where $R^{42}$ is a hydrogen atom is reacted with an alcohol compound of the formula $HOR^{55}$ ($R^{55}$ is a $C_1$–$C_3$ alkyl group or a group

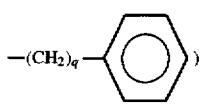

in the presence of an acid or a base or in the presence of an esterifying condensation agent, or such a process in which the corresponding compound (I) where $R^{42}$ is a hydrogen atom is converted into an acid halide by reaction with a halogenating agent such as thionyl chloride or phosphorus pentachloride, followed by the reaction of the resulting halide with an alcohol of the formula $HOR^{55}$ ($R^{55}$ is as defined above).

To synthesize such an amino acid derivative of the formula (I) in which $R^5$ is a group

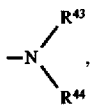

it is possible to use a process comprising a general amidating reaction, including, for example, such a process in which a corresponding compound of the formula (I) where $R^5$ is a group $-OR^{42}$ ($R^{42}$ is as defined above) is reacted with an amine of the formula

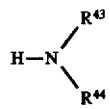

($R^{43}$ and $R^{44}$ are as defined above), or such a process in which the corresponding compound of the formula (I) where $R^5$ is a group $-OR^{42}$ is converted into an acid halide by reaction with a halogenating reagent such as thionyl chloride or phosphorus pentachloride, followed by the reaction of the resulting halide with an amine of the formula

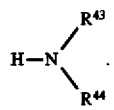

According to a second aspect of the present invention, there is also provided an immunomodulating agent which comprises as active ingredient at least one of a novel amino acid derivative represented by the general formula (I) or salts thereof.

The novel amino acid derivatives of the general formula (I) have a characteristic feature of their action that they stimulate specifically the proliferation of the activated T cells obtained from mouse spleen cells but do not act on the resting T cells. For example, the amino acid derivatives of this invention stimulate the proliferation of such T cells which have been treated with Concanavalin A, or the proliferation of such T cells which co-exist with macrophages. In view of this, the amino acid derivatives of the general formula (I) are expected to modulate the immunological activities of a living mammal owing to that they can increase and activate the clones of helper T cells or effecter T cells. Thus, the amino acid derivative of the formula (I) have potential utility that they are useful as therapeutics and/or preventives for tumors, auto-immune diseases, hematopoietic disorders and the like.

The activities of the novel amino acid derivative of the general formula (I) to stimulate the proliferation of T cells will be demonstrated by the following test.

Test 1

Effects of the novel amino acid derivatives of the general formula (I) on the proliferation of T cells were investigated by the following procedure.

The spleens, which had been excised in sterility from female Fisher 344 rats (12–16 weeks old, purchased from CHARLES RIVER JAPAN, INC), were squeezed in RPMI 1640 medium (a product of NISSUI PHARMACEUTICAL CO., LTD.) supplemented with 10% of fetal bovine serum, followed by passage of the resulting cell suspension through a column containing nylon wool fibres, whereby a cell suspension containing an abundant amount of T cells was obtained. This cell suspension was diluted to a level of $1\times10^6$ cells/ml with addition of a medium of the same composition as above. The cell-containing medium so obtained was then added with 5 μg/ml of Concanavalin A (product of Pharmacia AB), followed by incubation at 37° C. for 4 hours. Four hours later, α-methylmannoside was added to the incubated medium to give a concentration of 20 mg/ml of α-methylmannoside. After stirring the medium, cells were separated and collected therefrom by centrifugation. The collected cells were suspended at a level of $3\times10^6$ cells/ml in a medium of the same composition as above, followed by placing the resulting cell suspension in 100 μl portions in a 96-well microplate.

Novel amino acid derivatives at various concentrations, which are shown in Table 4, were incorporated in an amount of 100 μl as the test compounds to the respective cell suspensions in the plate, followed by incubation at 37° C. for 3 days in an incubator under air atmosphere containing 5% of carbon dioxide. Meanwhile, eighteen hours before the completion of the incubation, a solution of 10μ Ci/ml of radioactively labeled thymidine (Thymidine "6-$^3$H", a product of NEN Company) was added in an amount of 10 μl to the cell suspensions under incubation. The cells after the incubation were collected on a filter paper by means of a cell harvester, washed with water and radioactivity of the cells so treated was determined by a liquid scintillation counter. The determined values of the radioactivity of the cells as treated with the test compounds were evaluated on the assumption that the determined value of the radioactivity of the cells untreated, namely tested without addition of the test compound during the incubation of cells was amounting to 100. The so evaluated values are recorded and expressed as rates (%) for stimulating the T cell proliferation which show such extent that the proliferation of T cells is enhanced by the new amino acid derivative of this invention. The test results obtained are shown in Table 4 below.

From the results of Table 4, it is evident that the compounds of the general formula (I) according to this invention have excellent activity of stimulating the proliferation of T cells and hence have excellent activities for immunomodulation.

TABLE 4

| Activity of new amino acid derivatives for stimulating T cell proliferation | | |
|---|---|---|
| Compound No. | Concentration of compound (μg/ml) | Rate of stimulating proliferation of T cells (%) |
| 1 | 10 | 332 |
|   | 1 | 297 |
|   | 0.1 | 292 |
| 2 | 10 | 275 |
|   | 1 | 190 |

TABLE 4-continued

Activity of new amino acid derivatives for stimulating T cell proliferation

| Compound No. | Concentration of compound (µg/ml) | Rate of stimulating proliferation of T cells (%) |
| --- | --- | --- |
|  | 0.1 | 208 |
| 3 | 10 | 101 |
|  | 1 | 100 |
|  | 0.1 | 123 |
| 4 | 10 | 100 |
|  | 1 | 135 |
|  | 0.1 | 133 |
| 5 | 10 | 439 |
|  | 1 | 370 |
|  | 0.1 | 313 |
| 6 | 10 | 169 |
|  | 1 | 171 |
|  | 0.1 | 142 |
| 7 | 10 | 323 |
|  | 1 | 222 |
|  | 0.1 | 240 |
| 8 | 10 | 372 |
|  | 1 | 226 |
|  | 0.1 | 251 |
| 9 | 10 | 196 |
|  | 1 | 157 |
|  | 0.1 | 175 |
| 10 | 10 | 251 |
|  | 1 | 201 |
|  | 0.1 | 231 |
| 11 | 10 | 100 |
|  | 1 | 392 |
|  | 0.1 | 394 |
| 12 | 10 | 242 |
|  | 1 | 185 |
|  | 0.1 | 265 |
| 13 | 10 | 465 |
|  | 1 | 352 |
|  | 0.1 | 405 |
| 14 | 10 | 443 |
|  | 1 | 335 |
|  | 0.1 | 356 |
| 15 | 10 | 442 |
|  | 1 | 349 |
|  | 0.1 | 350 |
| 16 | 10 | 201 |
|  | 1 | 239 |
|  | 0.1 | 200 |
| 17 | 10 | 245 |
|  | 1 | 273 |
|  | 0.1 | 201 |
| 18 | 10 | 427 |
|  | 1 | 355 |
|  | 0.1 | 268 |
| 19 | 10 | 251 |
|  | 1 | 310 |
|  | 0.1 | 289 |
| 20 | 10 | 261 |
|  | 1 | 227 |
|  | 0.1 | 153 |

Further, according to a third aspect of the present invention, there is also provided an antitumor agent which comprises as active ingredient at least one of the new amino acid derivative represented by the general formula (I) or a salt thereof.

The antitumor activity of the novel amino acid derivatives of the general formula (I) will be demonstrated by the following test.

Test 2

The antitumor activity of some amino acid derivatives of the general formula (I) according to this invention was tested in the following manner. A suspension of Ehrlich ascites carcinoma cells was subcutaneously injected to one of the inguinal parts of each ICR mouse to transplant $4 \times 10^6$ cells/mouse. From the seventh day after the transplantation, a test compound was intraperitoneally injected daily for 7 days at a dose of 50, 5 or 0.5 mg/kg (4 mice per treated group of mice, but 8 mice per untreated control group of mice). On the fifteenth day after the transplantation, a solid cancer was cut out and weighed. A reduction in the weight of solid cancers of the mice in each treated group of mice which was evaluated in comparison with the control group is expressed as rate of inhibiting the tumor growth (%) in Table 5 below. As is presented in Table 5, each compound of the present invention exhibited remarkable activity for inhibition of tumor growth against mouse which solid cancer.

TABLE 5

| Compound No. of Invention | Dose (mg/kg) | Tumor growth inhibiting rate, % |
| --- | --- | --- |
| 10 | 5 | 31 |
| 10 | 50 | 58 |
| 12 | 0.5 | 37 |
| 19 | 5 | 12 |

Further, according to a fourth aspect of the present invention, there is also provided a hematopoietic stem cell amplifier which comprises as active ingredient at least one of the novel amino acid derivative represented by the general formula (I) or a salt thereof.

The novel amino acid derivatives have such another characteristic feature of their activities that they have property to stimulate the proliferation of T cells and also physiological activities of T cells. These amino acid derivatives also show an activity to stimulate production of interleukin-3 (IL-3) and interleukin-6 (II-6) from T cells [see "Zoketsu Inshi—Kenkyu no Choryu (in English: Hematopoietic Factors—Trend of Research)", compiled and edited by Miura Yoshisada and published from the Chugai Igakusha, Inc. (1991)]. Cytokines as these interleukins are known to exhibit an activity for stimulating the proliferation and differentiation of hematopoietic stem cells. Because the amino acid derivatives of the general formula (I) according to this invention show the activities to stimulate the proliferation of hematopoietic stem cells, they are expected to be useful as therapeutics for treating leukopenia, trombocytopenia and the like.

The activity of the novel amino acid derivatives of the general formula (I) for inducing proliferation of hematopoietic stem cells will be demonstrated by the following test.

Test 3

The activity of some amino acid derivatives of the general formula (I) according to this invention which induces proliferation of hematopoietic stem cells was tested in the following manner. Thus, bone-marrow cells had been prepared from the femurs of male BALB/c mouse (6–7 weeks old), and then a suspension of the bone-marrow cells was overlayed on "Lympholite M" (product of Cefalane Company), followed by centrifugation under 1500 g for 20 minutes. A lymphocyte fraction was collected, washed three times with "alpha MEM medium" (product of Gibco Company), and then diluted and suspended in the same medium as above to give a lymphocyte concentration of $7 \times 10^6$ cells/ml.

50 ml of the resulting cell suspension, 50 µl of a solution of a test compound in physiological saline, 50 µl of a culture supernatant of WEHI-3, 100 µl of phosphate-buffered physiological saline, 50 µl of a pre-deionized 10% bovine serum albumin solution, 50 µl of an L-asparagin solution (200 µg/ml), 50 µl of a calcium chloride solution (260 µg/ml) and 50 µl of bovine plasma containing sodium citrate were combined together. The liquid mixture so obtained was poured in portions of 50 μl/well on a slide glass ("Glass Ware", product of Flaw Laboratory Company). After coagulation of the mixture, the slide glass bearing the coagulated masses was immersed in 10% FBS-added alpha MEM medium, followed by incubation at 37° C. under 5% $CO_2$ for 7 days.

After completion of the incubation, the cells on the slide glass were immobilized with a 25% glutaraldehyde solution. In accordance with the methods proposed by Nagasawa et al. ["Zoketsu Kan Saibo (Hematopoietic Stem Cells)" compiled by takahisa Shimamaro, page 128 (The Nishimura Shoten Co., Ltd.)], the immobilized cells were stained for acetylcholinesterase activity which is specific for mouse megakaryocytes, and also the cells were stained with Mayer hematoxylin. Each cell culture so stained was dried and then sealed with a sealing agent. Under a microscope of ×100 magnification, the number of megakaryocytic colonies (i.e., the number of cells stained in an orange color) per well was counted. The results are presented in Table 6. As is shown in Table 6, it is evident that the compounds according to the present invention significantly increase the number of colonies of megakaryocytes, in other words, significantly stimulate the formation of megakaryocyte colonies and hence exhibit a remarkable activity to induce proliferation of hematopoietic stem cells.

TABLE 6

Activity of new amino acid derivatives for stimulating the formation of colonies of megakaryocytes

| Compound No. of Invention | Concentration of test compound (μg/ml) | Number of colonies of megakaryocytes (%) |
|---|---|---|
| No addition | 0 | 100 |
| 1 | 5 | 147 |
| 2 | 5 | 122 |
| 5 | 50 | 178 |
| 6 | 5 | 126 |
| 7 | 50 | 166 |
| 8 | 5 | 111 |
| 9 | 50 | 145 |
| 10 | 5 | 138 |
| 11 | 5 | 150 |
| 12 | 5 | 105 |
| 13 | 5 | 177 |
| 14 | 5 | 167 |
| 15 | 50 | 135 |
| 16 | 50 | 143 |
| 17 | 5 | 107 |
| 18 | 5 | 146 |
| 19 | 50 | 156 |
| 20 | 5 | 129 |
| 22 | 5 | 108 |
| 23 | 5 | 144 |
| 24 | 5 | 136 |
| 25 | 50 | 156 |
| 26 | 5 | 136 |
| 27 | 50 | 143 |
| 28 | 5 | 121 |
| 29 | 50 | 121 |

In addition, in order to evaluate toxicity of the amino acid derivatives of the formula (I) according to this invention to mammals, the representative examples of the amino acid derivatives of this invention listed in Table 1a to Table 1b were orally administered at a dose of 500 mg/kg to mice. The compounds so tested did not show any toxicity to mice, indicating that the novel amino acid derivatives (I) of this invention has low acute toxicity.

The novel amino acid derivative of the general formula (I) according to this invention can be administered in the form of a composition comprising said derivative as active ingredient and also a pharmaceutically acceptable, solid or liquid carrier so that said composition is given as antitumor agents, immunomodulating agents or hematopoietic stem cell-amplifying agents. The form of formulation of these medicaments may be chosen to be any of preparations which are administerable orally, rectally or parenterally. Described specifically, the new compounds of this invention can be formulated into injections, tablets, capsules, fine granules, syrups, suppositories, ointments and the like. The usable carriers, which can be incorporated in the compositions for antitumor agents, immunomodulators and hematopoietic stem cell amplifiers according to this invention, may include an organic or inorganic, solid or liquid carrier which is suited for oral, rectal or other parenteral administration, and which is generally inert and is pharmaceutically acceptable. Specific examples of such carriers include crystalline cellulose, gelatin, lactose, starch, magnesium stearate, talc, vegetable or animal fats and oils, gum, and polyalkylene glycols.

In the composition for the antitumor agent, immunomodulator or hematopoietic stem cell amplifier according to this invention, the proportion of the compound (I) of the present invention relative to the associated carrier can vary in a range of from 0.2% to 100% by weight. Further, the composition for the antitumor agent, immunomodulator or hematopoietic stem cell amplifier according to this invention can contain any other antitumor agent, immunomodulator, hematopoietic stem cell amplifier or other medicaments which is compatible with the compound of the present invention. In this case, needless to say, the novel amino acid derivative (I) according to this invention may not necessarily be a principal ingredient in the composition prepared.

The amino acid compound of the general formula (I) according to this invention can be administered at such a dosage that its desired action can be achieved generally without showing side-effects. Its specific dose should be determined under the physician's own judgment. In general, however, it may usually be administered at a dose of 1 mg to 10 g, preferably about 2 mg to 5 g per adult for the purposes of antitumor, immunomodulating or hematopoietic stem cell-amplifying treatments. Incidentally, the composition for the antitumor agent, immunomodulator or hematopoietic stem cell amplifier according to this invention can be administered in the form of pharmaceutical preparation units containing the amino acid compound of the general formula (I) in an amount of 1 mg to 5 g, preferably 3 mg to 1 g as an active ingredient.

It is to be noted that further subjects of the present invention embrace a use of the novel amino acid derivative of the general formula (I) or a salt thereof for the manufacture or formulation of an antitumor agent, immunomodulator or hematopoietic stem cell amplifier.

The present invention will next be described particularly with reference to Examples for production of certain compounds of this invention.

EXAMPLE 1

Synthesis of Compound No. 1

3-Methylvaleric acid (0.35 g) and α-methylserine benzyl ester (0.63 g) were dissolved in 10 ml of dimethylformamide (DMF). The resultant solution was added with 0.40 g of 1-hydroxybenzotriazole and 0.60 g of dicyclohexylcarbodiimide (DCC) and was then stirred at room temperature for 4 hours. The resulting reaction mixture was filtered to eliminate insoluble matter and the filtrate so obtained was concentrated under reduced pressure. The residue was added with 100 ml of chloroform. After the resulting solution was washed with 1N hydrochloric acid, chloroform was distilled off under reduced pressure to concentrate the solution. The residue so obtained was subjected to column chromatography with silica gel as a solid support, followed by elution with chloroform. Fractions containing the target compound were collected and the solvent was then distilled off, whereby 80 mg of the benzyl ester (Compound No. 2) of target Compound No. 1 were obtained (yield: 8.7%).

Compound No. 2 so obtained (80 mg) was dissolved in 5 ml of methanol and reduced in the presence of 10 mg of 10% palladium-carbon at room temperature for 4 hours under a hydrogen atmosphere. The resulting reaction mixture was filtered and the solvent was distilled off, affording 50 mg of target Compound No. 1 (yield: 88.5%).

EXAMPLE 2
Synthesis of Compound No. 3

α-Methylserine (0.6 g) was dissolved in 1 ml of a 28% methanolic solution of sodium methoxide, followed by the addition of 0.47 ml of γ-valerolactone. The resultant mixture was heated on oil bath and refluxed for 4 hours with stirring. After completion of the reaction, the solvent was distilled off from the reaction mixture under reduced pressure. The residue was added with a saturated aqueous NaCl solution. The mixture so obtained was acidified with dilute hydrochloric acid and then extracted four times with 30-ml portions of n-butanol. The resulting extracts were concentrated under reduced pressure and the residue was subjected to column chromatography with silica gel as a solid support. Elution was conducted with ethyl acetate containing 10% of methanol, so that the relevant fractions were collected. The solvent was removed from those fractions, whereby 80 mg of target Compound No. 3 were obtained (yield: 5.8%). As a by-product, 21 mg of the n-butyl ester (Compound No. 4) of target Compound No. 3 were also obtained (yield: 2.0%).

EXAMPLE 3
Synthesis of Compound No. 5

3-Hydroxybutyric acid (0.33 g) and O-benzyl-α-methylserine benzyl ester (1.25 g) were dissolved in 10 ml of DMF, followed by the addition of 0.56 g of 1-hydroxybenzotriazole and 0.83 g of dicyclohexylcarbodiimide (DCC). The resulting mixture was stirred at room temperature for 5 hours. The reaction mixture so obtained was filtered, and after removal of insoluble matter, the filtrate obtained was concentrated under reduced pressure. The residue was subjected to column chromatography with silica gel as a solid support. Elution was conducted with n-hexane containing 50% of ethyl acetate, whereby 120 mg of the benzyl ester derivative (Compound No. 6) of target Compound No. 5 were obtained (yield: 12.8%).

Compound No. 6 so obtained (100 mg) were dissolved in 15 ml of methanol and reduced in the presence of 10% palladium-carbon with stirring at room temperature for 16 hours under a hydrogen atmosphere (2.5 atm). The resulting reaction mixture was filtered and the solvent was distilled off from the filtrate, affording 50 mg of target Compound No. 5 (yield: 91.1%).

EXAMPLE 4
Synthesis of Compound No. 7

The reaction and processing treatments were conducted in a similar manner to Example 1 except that 0.35 g of 2-hydroxy-3-methylbutyric acid was used in place of 3-methylvaleric acid employed in Example 1, whereby 0.28 g of the benzyl ester (Compound No. 8) of target Compound No. 7 were obtained (yield: 30.1%). Compound No. 8 so obtained (80 mg) was catalytically reduced as in Example 1, yielding 40 mg of target Compound No. 7 (yield: 70.6%)

EXAMPLE 5
Synthesis of Compound No. 9

Leucine (0.91 g) was dissolved in 7 ml of a 1M ethanolic solution of sodium ethoxide, followed by the addition of 0.40 g of 2-hydroxy-3,4-dimethyl-γ-butyrolactone. After the resultant mixture was heated on oil bath and refluxed for 2 hours with stirring, the solvent was removed from the resulting reaction mixture by distillation. The residue obtained was heated at 120° C. for 2 hours on oil bath and was then cooled. The resulting material was added with 15 ml of DMF and 1.2 ml of benzyl bromide, followed by stirring at room temperature for 16 hours. After completion of the reaction, the solvent was eliminated from the resulting reaction mixture under reduced pressure. The residue was subjected to column chromatography with silica gel as a solid support. Elution was conducted with a 1:1 mixed solvent of ethyl acetate and n-hexane, whereby 0.46 g of the benzyl ester (Compound No. 10) of target Compound No. 9 was obtained (yield: 37.7%).

Compound No. 10 so obtained (0.16 g) was dissolved in 30 ml of methanol, followed by the reduction in the presence of 10 mg of 10% palladium-carbon, at room temperature under a hydrogen atmosphere for 3 hours. The reaction mixture obtained was filtered and the solvent was distilled off from the filtrate under reduced pressure, affording 0.11 g of target Compound No. 9 (yield: 92.2%).

EXAMPLE 6
Synthesis of Compound No. 11

The reactions and processing treatments were conducted in a similar manner to Example 5 except that 0.74 g of serine was used instead of leucine employed in Example 5, whereby 0.35 g of the benzyl ester (Compound No. 12) of target Compound No. 11 was obtained (yield: 31.0%). Compound No. 12 so obtained (150 mg) was catalytically reduced as in Example 5, whereby 104 mg of target Compound No. 11 were obtained (yield: 98.1%).

EXAMPLE 7
Synthesis of Compound No. 13

The reactions and processing treatments were conducted in a similar manner to Example 5 except that 0.84 g of α-methylserine was used in lieu of leucine employed in Example 5 and 0.46 g of pantolactone was used in place of 2-hydroxy-3,4-dimethyl-γ-butyrolactone, whereby 0.19 g of the benzyl ester (Compound No. 15) of target Compound No. 13 was obtained (yield: 15.6%). Compound No. 15 so obtained (150 mg) was catalytically reduced as in Example 5, whereby 105 mg of target Compound No. 13 were obtained (yield: 92.3%).

EXAMPLE 8
Synthesis of Compound No. 14

The reactions and processing treatments were conducted in a similar manner to Example 5 except that 0.84 g of α-methylserine was used instead of leucine employed in Example 5 and 0.46 g of pantolactone was used in place of 2-hydroxy-3,4-dimethyl-γ-butyrolactone and 0.5 g of methyl iodide was used in place of benzyl bromide. Thus, 0.13 g of target Compound No. 14 was obtained (yield: 14.3%).

EXAMPLE 9
Synthesis of Compound No. 16

The reactions and processing treatments were conducted in a similar manner to Example 5 except that 0.84 g of α-methylserine was used instead of leucine employed in Example 5 and 0.55 g of 2-hydroxy-3-methyl-4-isopropyl-

EXAMPLE 10
Synthesis of Compound No. 18

γ-butyrolactone was used in lieu of 2-hydroxy-3,4-dimethyl-γ-butyrolactone, whereby 290 mg of the benzyl ester (Compound No. 17) of target Compound No. 16 were obtained (yield: 11.4%). Compound No. 17 so obtained (170 mg) was catalytically reduced as in Example 5, affording 100 mg of target Compound No. 16 (yield: 81.0%)

EXAMPLE 10
Synthesis of Compound No. 18

The reactions and processing treatments of Example 5 were repeated similarly except that 0.94 g of s-methylcysteine was used instead of leucine employed in Example 5 and 1.0 g of methyl iodide in place of benzyl bromide. Thus, 30 mg of target Compound No. 18 were obtained (yield: 3.2%).

EXAMPLE 11
Synthesis of Compound No. 19

The reactions and processing treatments of Example 5 were repeated similary except that 0.94 g of s-methylcysteine was used instead of leucine employed in Example 5. Thus, 0.54 g of target Compound No. 19 were obtained (yield: 43.8%).

EXAMPLE 12
Synthesis of Compound No. 20

The reactions and processing treatments were conducted in a similar manner to Example 5 except that 1.0 g of s-benzylcysteine was used instead of leucine employed in Example 5. In this way, 0.78 g of the aimed Compound No. 20 were obtained (yield: 52.1%).

EXAMPLE 13
Synthesis of Compound No. 23

The reactions and processing treatments were conducted in a similar manner to Example 5 except that 0.75 g of threonine was used instead of leucine employed in Example 5, whereby 0.35 g of the benzyl ester (Compound No. 21) of the aimed Compound No. 23 was obtained (yield: 33.8%). Compound No. 23 so obtained (0.2 g) was reduced as in Example 5, whereby 55 mg of target Compound No. 23 were obtained (yield: 37.9%)

EXAMPLE 14
Synthesis of Compound No. 24

The reactions and processing treatments were conducted in a similar manner to Example 5 except that 0.55 g of alanine was used instead of leucine employed in Example 5, whereby 0.28 g of the benzyl ester (Compound No. 22) of target Compound No. 24 was obtained (yield: 29.5%). Compound No. 22 so obtained (0.2 g) was reduced as in Example 5, whereby 45 mg of target Compound No. 24 were obtained (yield: 32.1%).

EXAMPLE 15
Synthesis of Compound No. 26

The reactions and processing treatments were conducted in a similar manner to Example 5 except that 0.65 g of amino-isobutyric acid was used instead of leucine employed in Example 5, whereby 0.3 g of the benzyl ester (Compound No. 25) of target Compound No. 26 was obtained (yield: 30.5%). Compound No. 25 so obtained (0.2 g) was reduced as in Example 5, whereby 100 mg of target Compound No. 26 were obtained (yield: 69.4%).

EXAMPLE 16
Synthesis of Compound No. 27

α-Methylserine (0.3 g) was dissolved in a solution of 0.17 g of sodium ethoxide in 50 ml of ethanol, followed by the addition of 0.58 g of α-(N-carbobenzoxyamino)-γ-butyrolactone. The resulting mixture was heated on oil bath and refluxed for 4 hours under stirring. After completion of the reaction, the resulting reaction solution was distilled under reduced pressure to remove the solvent from the reaction solution. Water was added to the residue, followed by washing with ethyl ether. The resulting mixture as washed was acidified with 2N hydrochloric acid and was then extracted with ethyl acetate. The solvent was distilled off from the resultant extract under reduced pressure. The residue was added with a solution of 0.28 g of tetramethylammonium hydroxide pentahydrate in 30 ml of DMF, followed by the addition of 0.24 ml of benzyl bromide and then by the reaction at room temperature for 18 hours.

Water was added to the resulting reaction solution, followed by extraction with ethyl acetate. The solvent was distilled off and the residue was subjected to column chromatography with silica gel as a solid support. Elution was conducted with chloroform, the relevant fractions were collected and the solvent was then eliminated from the combined fractions, whereby 640 mg of the N-carbobenzoxylated derivative of the benzyl ester of target Compound No. 27 were obtained (yield: 57.7%).

The compound so obtained (400 mg) was dissolved in 100 ml of methanol and reduced in the presence of 0.1 g of 10% palladium-carbon at room temperature for 2 days under hydrogen gas at 4 kg/cm$^2$. The reaction mixture so obtained was then filtered and the solvent distilled off from the filtrate under reduced pressure, whereby 123 mg of target Compound No. 27 were obtained (yield: 62.1%).

EXAMPLE 17
Synthesis of Compound No. 29

The reactions and processing treatments were conducted in a similar manner to Example 5 except that 0.63 g of 3-aminobutyric acid was used in lieu of leucine employed in Example 5, whereby 0.41 g of the benzyl ester (Compound No. 28) of target Compound No. 29 was obtained (yield: 41.6%). Compound No. 28 so obtained (0.33 g) was reduced as in Example 5, whereby 200 mg of target Compound No. 29 were obtained (yield: 85.7%).

INDUSTRIAL UTILITY

The new amino acid derivatives of the general formula (I) provided in accordance with the present invention have an activity for stimulating the proliferation of T cells and show the effects to modulate the immunological activities of living mammals. The new amino acid derivatives also have antitumor activities and/or carcinostatic activities against various tumors and/or cancers. They also exhibit activities for stimulating both the proliferation and physiological activities of T cells, whereby consequently they act to stimulate the proliferation of hematopoietic stem cells. Accordingly, the novel amino acid derivatives according to this invention are useful as immunomodulators, antitumor agents, carcinostatic agents or hematopoietic stem cell amplifiers.

We claim:

1. An amino acid derivative having the formula

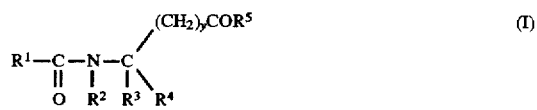

wherein $R^{1a}$ is a linear or branched alkyl group or a mono- or di-hydroxy-substituted linear or branched alkyl group selected from the group consisting of the alkyl groups and mono- or di-hydroxy-substituted alkyl groups which are represented by the formulae (i)–(iv):

(i) 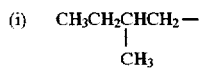

(ii) 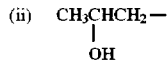

(iii) 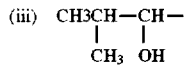

and (iv) 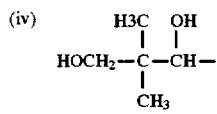

$R^{3a}$ is a group represented by the formula $-(CH_2)_cR^{14a}$ (where $R^{14a}$ is a hydroxyl group, a $C_1-C_3$ alkoxy group or an aralkyloxy group and c is an integer of 1, 2 or 3); $R^{4a}$ is a hydrogen atom or $C_1-C_3$ alkyl group, and $R^{5a}$ is a hydroxyl group, a $C_1-C_3$ alkoxy group or an aralkyloxy group.

2. An amino acid derivative according to claim 1, having the formula:

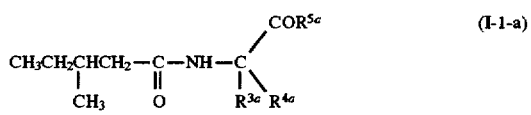 (I-1-a)

wherein $R^{3a}$ is a group represented by the formula $-(CH_2)_cR^{14a}$ (where $R^{14a}$ is a hydroxyl group, and c is an integer of 1, 2 or 3); $R^{4a}$ is a $C_1-C_3$ alkyl group, and $R^{5a}$ is a hydroxyl group, a $C_1-C_3$ alkoxy group or benzyloxy group.

3. An amino acid derivative according to claim 1, having the formula:

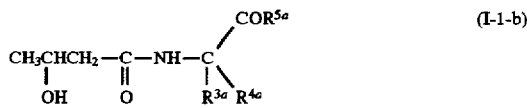 (I-1-b)

wherein $R^{3a}$ is a group represented by the formula $-(CH_2)_cR^{14a}$ (where $R^{14a}$ is a hydroxyl group, or a $C_1-C_3$ alkoxy group or benzyloxy group and c is an integer of 1, 2 or 3); $R^{4a}$ is a $C_1-C_3$ alkyl group, and $R^{5a}$ is a hydroxyl group, a $C_1-C_3$ alkoxy group or benzyloxy group.

4. An amino acid derivative according to claim 1 which has the formula

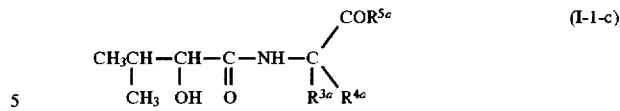 (I-1-c)

wherein $R^{3a}$ is a group represented by the formula $-(CH_2)_cR^{14a}$ (where $R^{14a}$ is a hydroxyl group, or a $C_1-C_3$ alkoxy group and c is an integer of 1, 2 or 3); $R^{4a}$ is a $C_1-C_3$ alkyl group, and $R^{5a}$ is a hydroxyl group, a $C_1-C_3$ alkoxy group or benzyloxy group.

5. An amino acid derivative according to claim 1 having the formula:

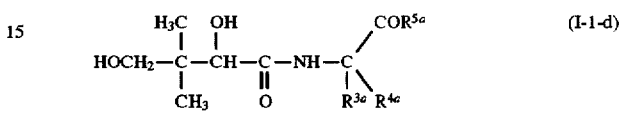 (I-1-d)

wherein $R^{3a}$ is a group represented by the formula $-(CH_2)_cR^{14a}$ (where $R^{14a}$ is a hydroxyl group, or a $C_1-C_3$ alkoxy group and c is an integer of 1, 2 or 3); $R^{4a}$ is a $C_1-C_3$ alkyl group, and $R^{5a}$ is a hydroxyl group, a $C_1-C_3$ alkoxy group or benzyloxy group.

6. A pharmaceutical composition comprising as the active ingredient an amount of the amino acid derivative selected from the group consisting of an amino acid derivative (I-1) having the formula of claim 1, an amino acid derivative having the formula (I-1-a) of claim 2, an amino acid derivative having the formula (I-1-b) of claim 3, an amino acid derivative having the formula (I-1-c) of claim 4, and an amino derivative having the formula (I-1-d) of claim 5 effective for use as an immunomodulator, an antitumor agent or a hematopoietic stem cell-amplifying agent, in association with a pharmaceutically acceptable carrier for the active ingredient.

7. A compound of the formula

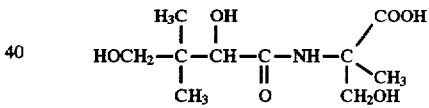

or a pharmaceutically acceptable salt, methyl ester or benzyl ester thereof.

* * * * *

UNITED STATES PATENT AND TRADEMARK OFFICE
CERTIFICATE OF CORRECTION

PATENT NO. : 5,798,387
DATED : August 25, 1998
INVENTOR(S) : ISHIZUKA et al

It is certified that error appears in the above-indentified patent and that said Letters Patent is hereby corrected as shown below:

Column 32, claim 1, line 60, change " 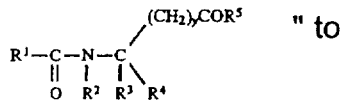 " to

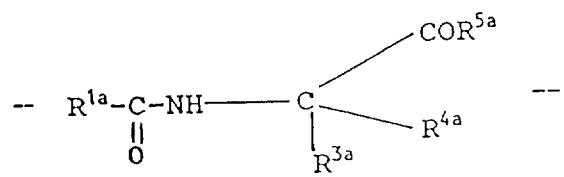 --

Signed and Sealed this

Fifth Day of January, 1999

Attest:

Attesting Officer

*Acting Commissioner of Patents and Trademarks*